United States Patent [19]
Lanza et al.

[11] Patent Number: 5,138,553
[45] Date of Patent: Aug. 11, 1992

[54] METHOD AND APPARATUS FOR BONE MINERAL MEASUREMENT USING A MEASUREMENT REGION DEFINED AT A SELECTED DISTANCE FROM A STYLOID BONE TIP

[75] Inventors: Richard C. Lanza, Brookline; Joseph R. Votano, Tewksbury, both of Mass.

[73] Assignee: Expert Image Systems, Inc., Somerville, Mass.

[21] Appl. No.: 321,764

[22] Filed: Mar. 10, 1989

[51] Int. Cl.$^5$ .................... G06F 15/42; A61B 6/00
[52] U.S. Cl. .................... 364/413.26; 378/53; 378/55
[58] Field of Search .................... 364/518, 413.26; 378/53, 55, 87, 201

[56] References Cited

U.S. PATENT DOCUMENTS

| | | | |
|---|---|---|---|
| 4,663,772 | 5/1987 | Mattson et al. | 378/201 |
| 4,721,112 | 1/1988 | Hirano et al. | 378/53 |
| 4,768,214 | 8/1988 | Bjorkholm | 378/87 |
| 4,788,429 | 11/1988 | Wilson | 378/53 |
| 4,799,247 | 1/1989 | Annis et al. | 378/87 |
| 4,829,549 | 5/1989 | Vogel et al. | 378/55 |
| 4,833,625 | 5/1989 | Fisher et la. | 364/518 |
| 4,837,686 | 6/1989 | Sones et al. | 364/413.19 |
| 4,864,594 | 9/1989 | Inbar et al. | 378/4 |

OTHER PUBLICATIONS

R. A. Schlenker et al., *Calcif. Tiss. Res.*, vol. 20, pp. 41-52 (1976).
Ross et al., *J. Bone & Mineral Res.*, vol. 3, pp. 1-11 (1988).
L. Nilas et al., *J. Nuclear Med.*, vol. 26, pp. 1257-1262 (1985).
B. J. Aubrey et al., *J. Orthopaedic Res.*, vol. 2, pp. 314-321 (1984).
J. B. Christensen et al., *Anta Rec.*, vol. 160, pp. 261-272 (1968).

*Primary Examiner*—Gail O. Hayes
*Attorney, Agent, or Firm*—Thomas J. Engellenner

[57] ABSTRACT

Methods and apparatus for precise and consistent selection of bone mineral content (BMC) measurement regions of selected bones, and accurate calculation of BMC from a displayed radiological image of the bones, calculate the position of the styloid tip of each bone, define a measurement region having selected positional correspondence to the position of the styloid tip, and sum pixel intensity values in the measurement region to yield a pixel intensity sum representative of bone mineral content. Bone density values are obtained by dividing the pixel intensity sum by a value representative of the areas of the measurement region, to yield a value representative of bone density. The position of the styloid tip is calculated by detecting selected transverse image edges, searching along the selected transverse image edges to determine a set of pixels which define extremities of the styloid tip, and defining a line substantially tangent to the styloid tip.

44 Claims, 7 Drawing Sheets

METHOD AND APPARATUS FOR BONE MINERAL MEASUREMENT USING A MEASUREMENT REGION DEFINED AT A SELECTED DISTANCE FROM A STYLOID BONE TIP

BACKGROUND OF INVENTION

This invention relates generally to techniques for measurement of bone mineral content, and, more particularly, relates to non-invasive methods and apparatus for accurate and consistent measurement of bone mineral content and density.

Methods for non-invasive measurement of bone mineral content (BMC) and density provide an important diagnostic technique in evaluating the state of an individual's bone structure, and particularly, in determining whether an individual suffers from osteoporosis, or is undergoing bone loss which can eventually lead to osteoporosis if not detected and controlled. Measurement of BMC values is especially important in older individuals, for evaluating the efficacy of treatment for osteoporosis.

One widely employed technique for measuring BMC at selected regions of bone is bone absorption densitometry, which involves measurement of the attenuation of radiation—such as X-rays— transmitted or scanned through a selected bone region in an individual. The magnitude of attenuation of the radiation is directly related to the quantity of bone mineral in the selected bone area, and attenuation values can be generated directly from radiological image data.

Bone tissue continually undergoes a remodeling process in which old bone dissolves and new bone forms in its place. The rate of this remodeling process depends upon the composition of the bone. Human bones, for example, are composed of two bone types, referred to as cortical bone and trabecular bone. Cortical bone has a relatively high density, and is found principally on the outer surface of bone structures. Trabecular or cancellous bone is porous, has a lower density than does cortical bone, and is found primarily in the core regions of bones. The amount of trabecular and cortical bone in the radius and ulna of the forearm, for example, has been well documented. See, for example, R. A. Schlenker et al, *Calcif. Tiss. Res.*, Vol. 20, pp. 41-52 (1976).

Because trabecular bone has a remodeling or turnover rate 7 to 8 times greater than that of cortical bone, the sensitivity of bone-loss detection increases in proportion to the percentage of trabecular bone in the measurement region. Sites with higher percentages of trabecular bone can therefore provide more accurate indications of the magnitude of bone loss. Trabecular BMC values are typically measured at several bone measurement sites to determine whether bone loss is occurring. These sites commonly include the lower vertebrae of the spine, including lumbar 1-3, the hip, the heel, and the distal area of the radius and ulna—i.e., the area closest to the wrist. Each of these bone sites contain varying amounts of trabecular and cortical bone.

In particular, the distribution of cortical and trabecular bone throughout the human skeletal system is inhomogeneous. The heel bone, Os Calcis, is 95% trabecular in content, while the intermediate regions of the radius and ulna contain 95%-96% cortical bone. The percentages of cortical and trabecular bone, moreover, can vary greatly in the same bone from one area to another. This variation limits the accuracy of conventional bone absorption densitometry, because cortical and trabecular bone have significantly different densities and thus different X-ray attenuation. Using Iodine-125 as an X-ray source, for example, the difference in transmitted 27 KeV photons through 1 mm of cortical bone and 1 mm of trabecular bone is approximately 28 percent. The varying amounts of cortical and trabecular bone in different regions of the same bone therefore cause spurious changes in calculated bone loss values when subsequent measurements are performed on different bone measurement regions.

While bone absorption densitometry has proven useful for generating estimates of BMC values, conventional bone absorption densitometry methods and apparatus are hampered by several sources of error which limit accuracy and resolution. These errors— which arise from variability in bone type from region to region, and the criteria utilized in selecting and defining bone measurement regions—are most apparent when practitioners attempt to evaluate bone loss over periods of months or years by correlating BMC values generated in different measurements or "scans".

Those skilled in bone absorption densitometry techniques have long recognized that precise definition of the selected bone measurement area is a prerequisite for accurate measurement of BMC. Practitioners have emphasized the need for defining and measuring the same bone area, without measurement region positioning error, in subsequent BMC scans. See, for example, Ross et al, *J. Bone & Mineral Res.*, Vol. 3, pp. 1-11, (1988); L. Nials et al, *J. Nuclear Med.*, Vol. 26, pp. 1257-1262 (1985); and B.J. Awbrey et al, *J. Orthopedic Res.*, Vol. 2, pp. 314-321 (1984). Conventional bone absorption densitometry techniques, however, have not provided a means for eliminating measurement region positioning errors.

It is therefore an object of the invention to provide bone absorption densitometry methods and apparatus which provide precise and consistent selection of BMC measurement regions.

The deficiencies of conventional bone absorption densitometry methods and apparatus are especially apparent in diagnosing the gradual bone loss which is characteristic of osteoporosis. Bone loss in women, for example, is approximately 0.5% per year prior to menopause. Following menopause, women can lose bone at approximately 1%-2% per year and, in some cases, at much higher rates. Therefore, in order to determine whether an individual has a bone loss problem, BMC measurement techniques must be capable of detecting bone loss as small as 1%. Conventional techniques for measuring BMC values generally fail to achieve this level of precision required for accurate diagnosis of osteoporosis, due to an inability to establish a consistent measurement region of bone which can be equivalently evaluated in scans performed months or years after the initial scan.

It is thus another object of the invention to provide such methods and apparatus which can accurately and consistently select the same measurement region during successive scans.

Certain conventional techniques for measurement of BMC values utilize a predetermined value of the interosseous distance between the radius and ulna to define a bone measurement area. This interosseous distance criterion is another source of error, because inaccurate measurement of the interosseous distance results in significant BMC measurement variance. An error of approximately 3% in measured BMC values can arise if an initial BMC measurement of the radius bone of the forearm is performed at a region where the radius and ulna are separated by 5 mm, and a subsequent BMC measurement is made at a region having an interosseous separation of 4 or 6 mm. See B. J. Awbrey et al, *J. Orthopaedic Res.*, Vol. 2, pp. 314–321 (1984). This error is due to the different cortical or trabecular bone percentages in the first and second measurement regions.

This interosseous distance, moreover, is not a constant, but instead is a variable which depends upon other parameters. For example, rotation of the wrist causes translation of the radius and ulna, resulting in variation of the interosseous distance. Rotation of the wrist, whether clockwise or counterclockwise, can occur even when the subject's wrist is clamped. This interosseous variability has been identified by a number of investigators in the field. See, for example, J.B. Christensen et al, *Anta Rec.*, Vol. 160, pp. 261–272 (1968).

In addition, the relative angular position of the forearm and upper arm, and the angular position of the humerus relative to the body, can have a significant effect on the interosseous distance. In view of the many possible variations and degrees of freedom in positioning a patient's forearm, and the varying level of expertise of the personnel executing a bone scan, it is highly unlikely that the same measurement region can be selected in a given instance on the basis of interosseous distance. It is still more unlikely that the same measurement region can be selected on this basis during successive scans over the course of time.

Those skilled in the art have long recognized this repositioning error, and the consequent inability to consistently select the same bone measurement region in successive scans.

It is therefore a further object of the invention to provide such methods and apparatus which can automatically correct repositioning errors and provide accurate correlation with previously measured BMC and other values.

Conventional BMC measurement methods provide no data representative of the exact position of the areas scanned by the x-ray source, relative to the imaged bone. Instead, the scanned area is correlated with the edges of each bone by utilizing an "edge criterion", under which a bone edge is "detected" when radiation attenuation has decreased by a selected percentage from the tissue baseline attenuation. This "edge criterion" limits sensitivity in identifying bone edges that are in close proximity. Moreover, such "edge criteria" are arbitrarily defined, and do not define measurement regions having high trabecular bone content—i.e., at least 60%—in the distal radius or ulna.

It is therefore a further object of the invention to provide bone absorption densitometry methods and apparatus which facilitate selection of measurement regions having high trabecular bone content.

It is still another object of the invention to provide such methods and apparatus which can be substantially automated, and which can be rapidly and easily utilized by an operator.

SUMMARY OF THE INVENTION

The foregoing objects are attained by the invention, which provides methods and apparatus for precise and consistent selection of BMC measurement regions of selected bones, and accurate calculation of BMC from a displayed radiological image of the bones, by calculating the position of the styloid tip of each bone, defining a measurement region having selected positional correspondence to the position of the styloid tip, and summing pixel intensity values in the measurement region to yield a pixel intensity sum representative of bone mineral content. Bone density values are obtained by dividing the pixel intensity sum by a value representative of the areas of the measurement region, to yield a value representative of bone density.

The position of the styloid tip can be calculated by detecting selected transverse image edges, searching along the selected transverse image edges to determine a set of pixels which define extremities of the styloid tip, and defining a line substantially tangent to the styloid tip.

The invention includes methods and apparatus for defining a baseline for the measurement region, the baseline being substantially parallel to, and separated by a selected distance from, the tangent line. Defining a measurement region can also include detecting outer and inner axial edges of the bone for selected axial distances from an origin point. The outer and inner edge positions can be used to compute transverse width values for the bone, at positions along the bone between points of minimum and maximum interosseous separation. The invention further includes methods and apparatus for defining a measurement region to have a selected axial dimension and to either include or exclude the inner and outer axial bone edges.

Another aspect of the invention includes methods and apparatus for defining the measurement region baseline by calculating ratios of axial-separation-from-tangent-line to width (AW ratios) at positions along the bone, and defining the baseline to be at a position having a selected AW ratio. The AW ratios can be selected to define a measurement area having maximum trabecular bone content.

A further aspect of the invention includes methods and apparatus for comparing a currently displayed image with a stored, previously displayed image to obtain a positional correlation of the bones in currently and previously displayed images. Axial and transverse correction factors can be calculated for correcting differences in Position of the bone in currently and previously displayed images, by comparing positions of the styloid tips in the currently and previously displayed images.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which.

DESCRIPTION OF PREFERRED EMBODIMENT

Figure 1A:
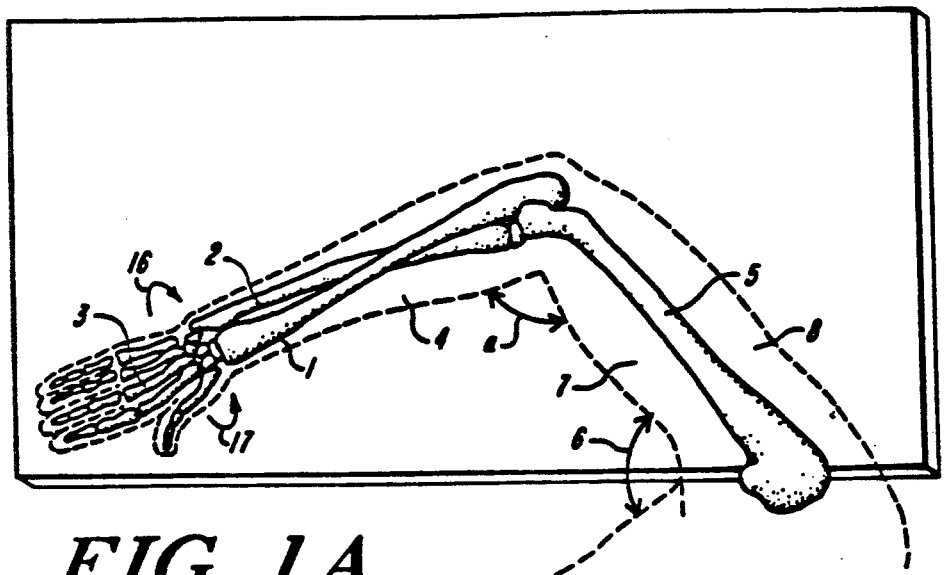
FIG. 1 depicts an imaged human arm and wrist joint, including the radius and ulna bones.
FIG. 1B depicts apparatus for radiological imaging of bone joints.
FIG. 1C depicts apparatus for processing data representative of imaged bone joints.

FIG. 1A is a schematic diagram depicting a typical radiological image which can be processed to derive measurements of bone mass and density. The image shows a human forearm 4, having a radius 1 and ulna 2. While the wrist joint, including radius 1 and ulna 2, is typically selected for bone density measurement, other joints and bones can be imaged and evaluated in accordance with the invention.

Figure 1B:
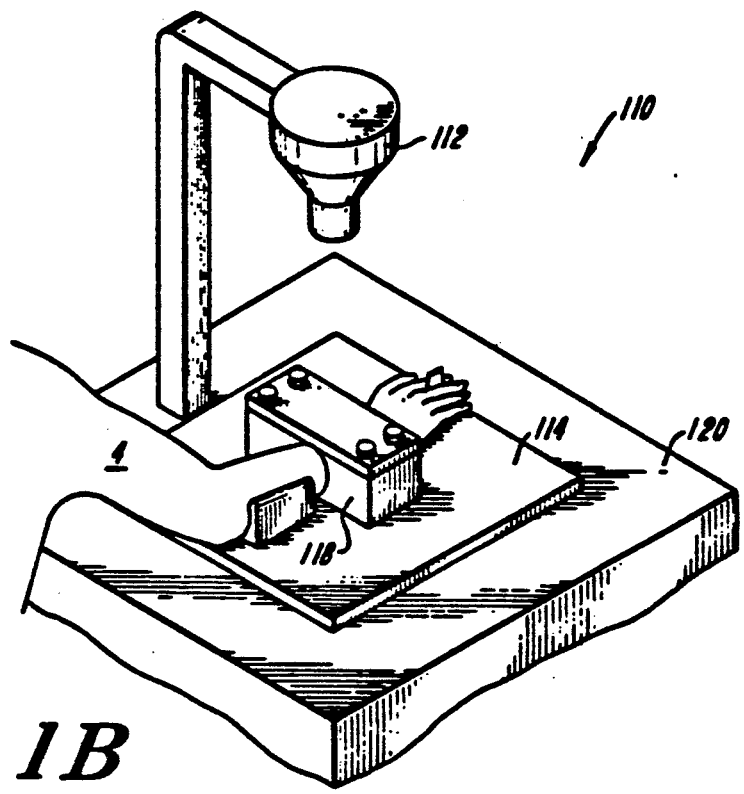
Figure 1C:
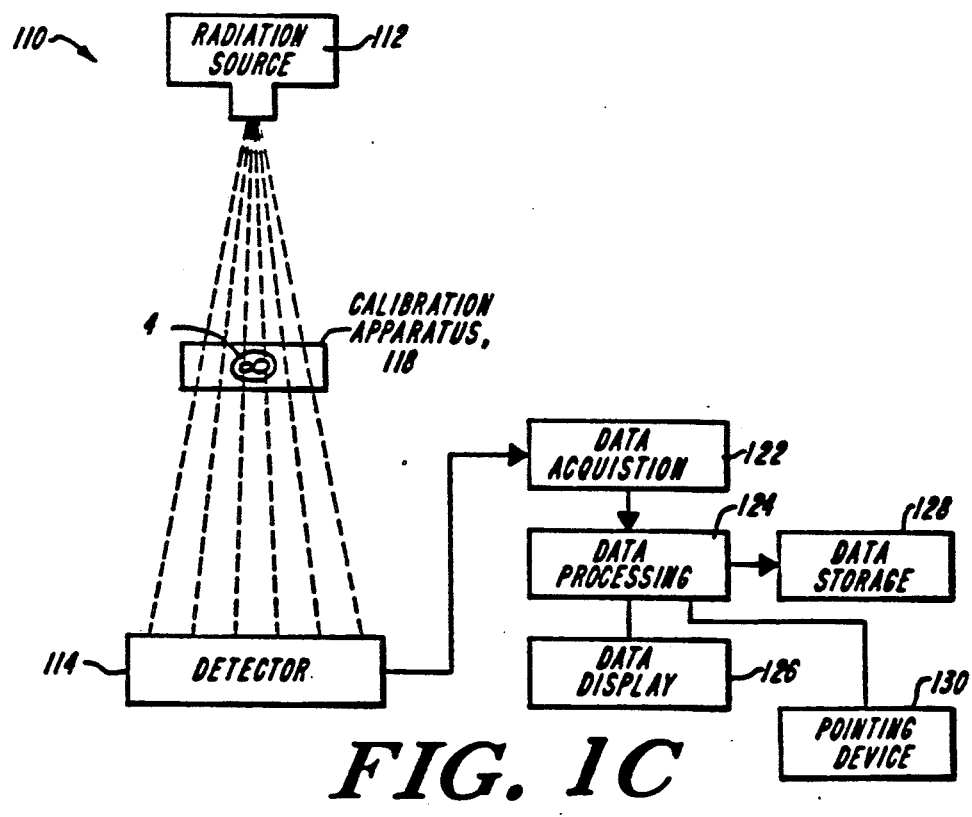

A bone joint image like that shown in FIG. 1A can be generated by conventional radiological imaging apparatus and processed in accordance with the invention. Preferably, however, such an image can be generated by the line scanning detector disclosed in commonly owned U.S. Patent Application entitled "Linear Radiation Detector" Ser. No. 322,085 filed on even date herewith and incorporated herein by reference, or the area scanning detector disclosed in commonly owned U.S. Patent Application entitled "Digital Readout System" Ser. No. 321,766 filed on even date herewith and incorporated herein by reference. Such apparatus 110 is depicted in FIG. 1B, including a radiation source 112, a detector 114, and a clamping device 118 for clamping the patient's arm 4 in a selected position between source 112 and detector 114. These elements, which form no part of the present invention, are described in greater detail in commonly owned U.S. Patent Application entitled "Source Filter for Radiographic Imaging" Ser. No. 321,989 filed on even date herewith and incorporated herein by reference. As depicted in FIG. 1C, such detectors can be coupled to a data acquisition module 122, as disclosed in commonly owned U.S. Patent Application entitled "Data Acquisition System for Radiographic Imaging" Ser. No. 321,994 filed on even data herewith and incorporated herein by reference.

In measuring bone mineral content (BMC) and bone mineral density (BMD) for the wrist, the patient's wrist can be clamped in a clamshell device 118 (depicted in FIGS. 1B and 1C) referred to as a bolus, which surrounds and immobilizes the wrist. The bolus can be conventional in design, or, preferably, can be constructed in accordance with the disclosure of commonly owned U.S. Patent Application entitled "Limb Positioning And Calibration Apparatus For Radiographic Imaging" Ser. No. 321,990 filed on even date herewith and incorporated herein by reference. When the wrist has been fixed, the upper arm and elbow are positioned so as to establish a selected angle 9 between the upper arm 10 and forearm 4, as indicated in FIG. 1A.

Figure 2:
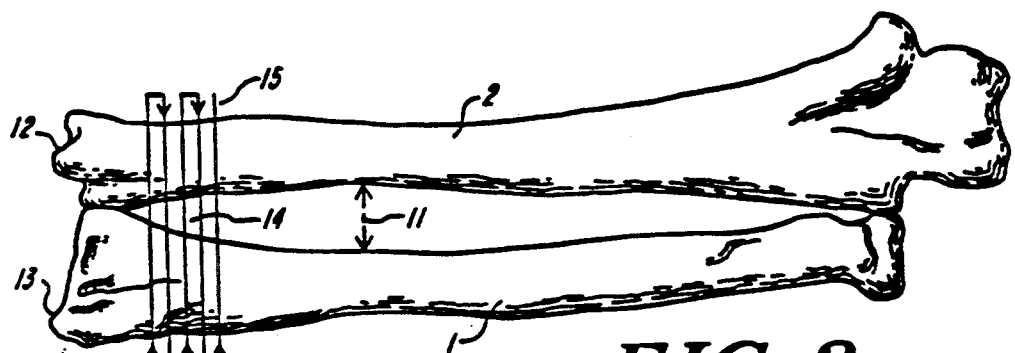
FIG. 2 depicts an image of a human radius and ulna generated by scanning the bones with an X-ray beam.
Figure 7D:
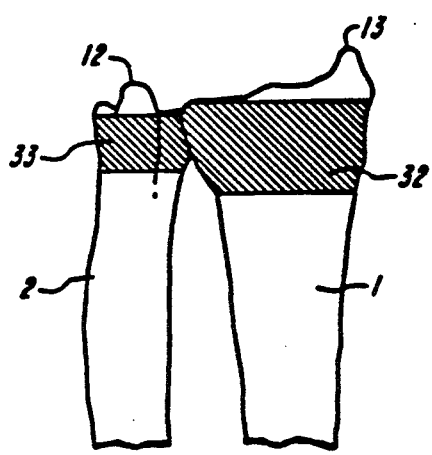
FIGS. 7D and 7E depict full width and narrowed measurement regions defined in accordance with another embodiment of the invention.
Figure 7E:
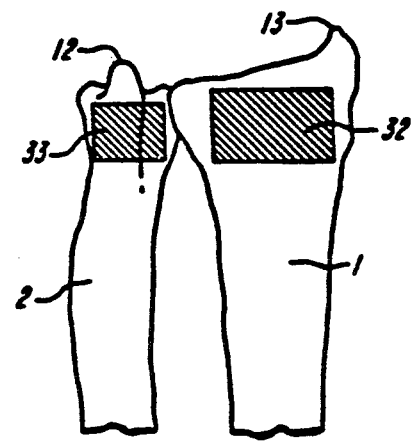

In typical prior art BMC measurement systems, a rectilinear scan, indicated in FIG. 2 by trace 15, is made across both the ulna 2 and radius 1 using a collimated x-ray source and a collimated detector (not shown) positioned on opposite sides of the wrist. The detector typically scans a 2–4 mm width of bone during each scan.

Typical prior art BMC measurement methods provide no data representative of the exact location of the areas scanned by the x-ray source. Instead, the scanned area is correlated with the edges of each bone by utilizing a selected attenuation value referred to as the "85% edge criterion", under which bone edge is indicated when the attenuation of the beam has dropped by 85% from the tissue baseline. This prior art "edge criterion" is used for measurements on the distal radius—i.e., the area of the radius closest to the wrist. In prior art methods, the actual attenuation value of the "edge criteria" may vary, depending upon the selected measurement region on the bone, and the patient being evaluated.

Once the bone edges have been determined by this criterion, the scanned area can be correlated by the interosseous distance 11. In particular, by utilizing a rectilinear scan 15 the position of the detector and radiation source are known, because the scan is preformed in predetermined steps across the bone. Accordingly, the position and intensity of radiation through the bone can be correlated, in principle, with selected locations in the bone. From this information and application of the "edge criterion" the separation between the radius and ulna can be found.

In practice, the prior art method involves a scan 15 of a region of the bone and an extrapolation of the determined interosseous distances to obtain the area of the bone at selected interosseous separations, to measure a bone area at the "5 mm interosseous site" 14. Thus, BMC values obtained by prior art methods are identified as being made at 1 mm, 5 mm, 6 mm, or 8 mm to indicate that the scanned area on the radius or ulna is located at a region having a selected separation distance between the ulna and radius.

However, as discussed above, typical prior art methods have serious deficiencies, including variations in interosseous distance with rotation of the wrist, inability to reposition the arm consistently from scan to scan, and a lack of BMC measurement sensitivity, arising from the application of the "edge criterion."

Accordingly, to provide consistent, repeatable selection of bone density measurement regions, and enhanced sensitivity in detection of bone loss in annual or semi-annual measurements, the invention utilizes the styloid tip of each bone as a reference point, and establishes measurement regions in selected regions that contain high percentages of trabecular bone, rather than cortical bone. These selected regions, in the case of the radius and ulna, have been determined to lie at specific distances from the respective styloid tips of these bones, as illustrated by FIGS. 3 and 4.

Figure 3:
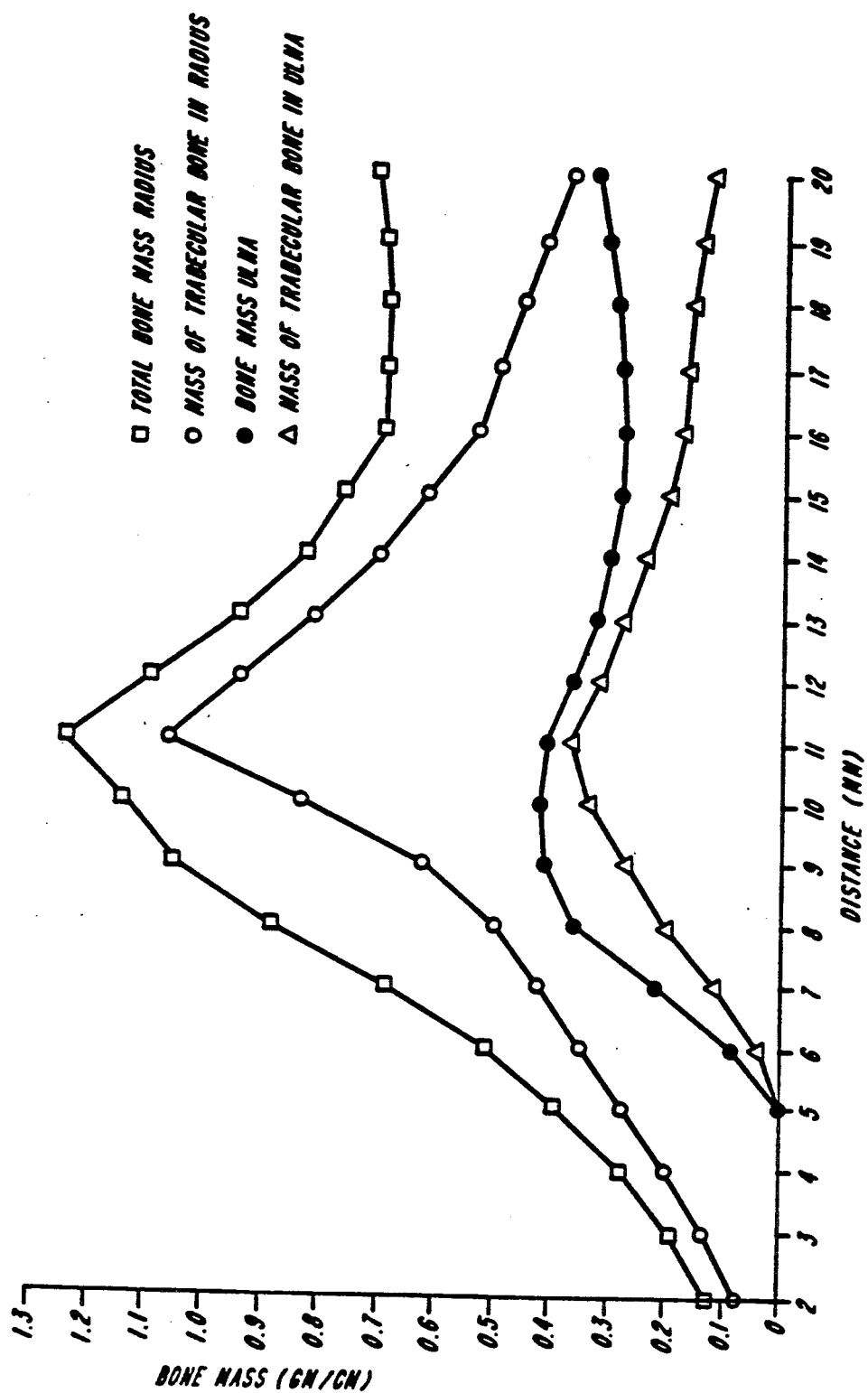
FIG. 3 is a graph of total and trabecular bone mass for radius and ulna vs. axial distance from the styloid tip of the radius bone, which is utilized in accordance with the invention as a reference point for measurement of radius and ulna.
Figure 4:
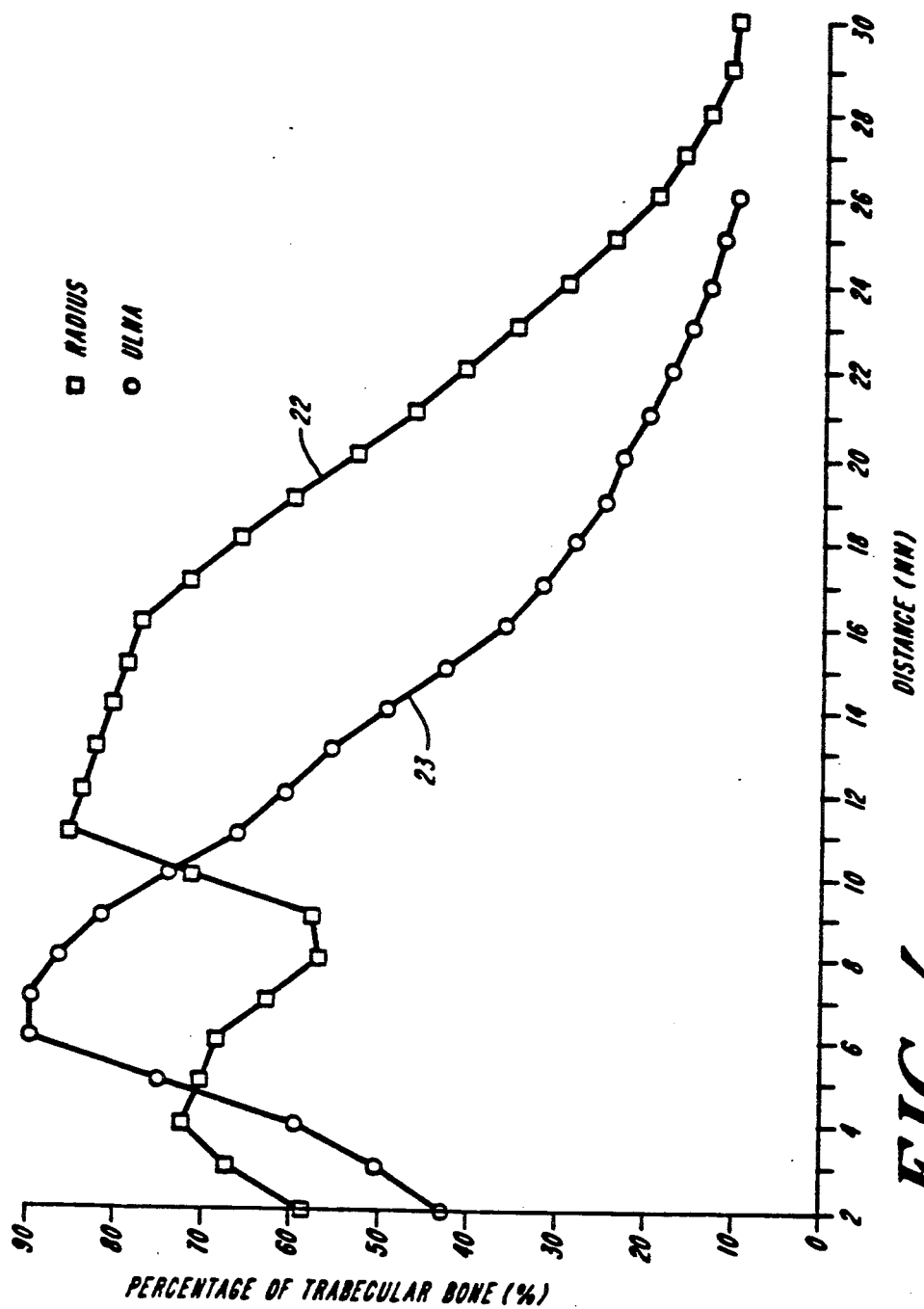
FIG. 4 is a graph of the percentage of trabecular bone for the radius and ulna vs. the distance from the respective styloid tip of each bone.

FIGS. 3 and 4 are graphs illustrating typical values for trabecular bone mass in the radius and ulna of a 43 year old woman, as a function of distance from the styloid tip of the radius and ulna, respectively. In particular, curves 18 and 20 of FIG. 2 show total bone mass, as a function of distance from the styloid tip, for the radius and ulna, respectively. Curves 19 and 21 illustrate trabecular bone mass in the radius and ulna, respectively, as a function of distance from the styloid tip of each bone. Curves 22 and 23 of FIG. 3 depict the percentage of trabecular bone mass for the radius and ulna, respectively, as a function of distance from the styloid tip of each bone. Although percentages and dimensional values may vary, depending upon the age of the patient and variations between individuals, we have found that if the position data are scaled as a percentage of the total length of the bone, the curves are extremely similar in shape.

In practice, to improve sensitivity in detecting bone loss, it is important to measure areas that contain high percentages of trabecular bone. Thus, in accordance with the invention, measurement regions are selected to contain 60% or more of trabecular bone. As indicated in FIG. 4, the percentage of trabecular bone present in the radius and ulna beyond 30 mm from the styloid tip of each bone drops below 10%, and the percentage of cortical bone for both the radius and ulna is approximately 95% at points beyond 40 mm from the styloid tip.

As FIG. 4 shows, the region associated with this 60% limit begins at 2 mm and 4 mm, respectively, from the styloid tip of the radius and ulna, respectively. The highest trabecular content is between approximately 9 mm and 20 mm from the styloid tip in the radius, and between approximately 4 mm and 12 mm from the styloid tip in the ulna. In accordance with the invention, therefore, BMC measurement regions are selected within these areas of high trabecular bone content, in a manner described in greater detail in connection with FIGS. 5a-5c. In addition, while measurement regions are preferably selected within areas of high trabecular bone content, the method set forth in FIGS. 5a-5c can be utilized to identify and evaluate areas containing high percentages of cortical bone, in regions beyond 4 cm from the styloid tip of each bone.

Figure 5A:
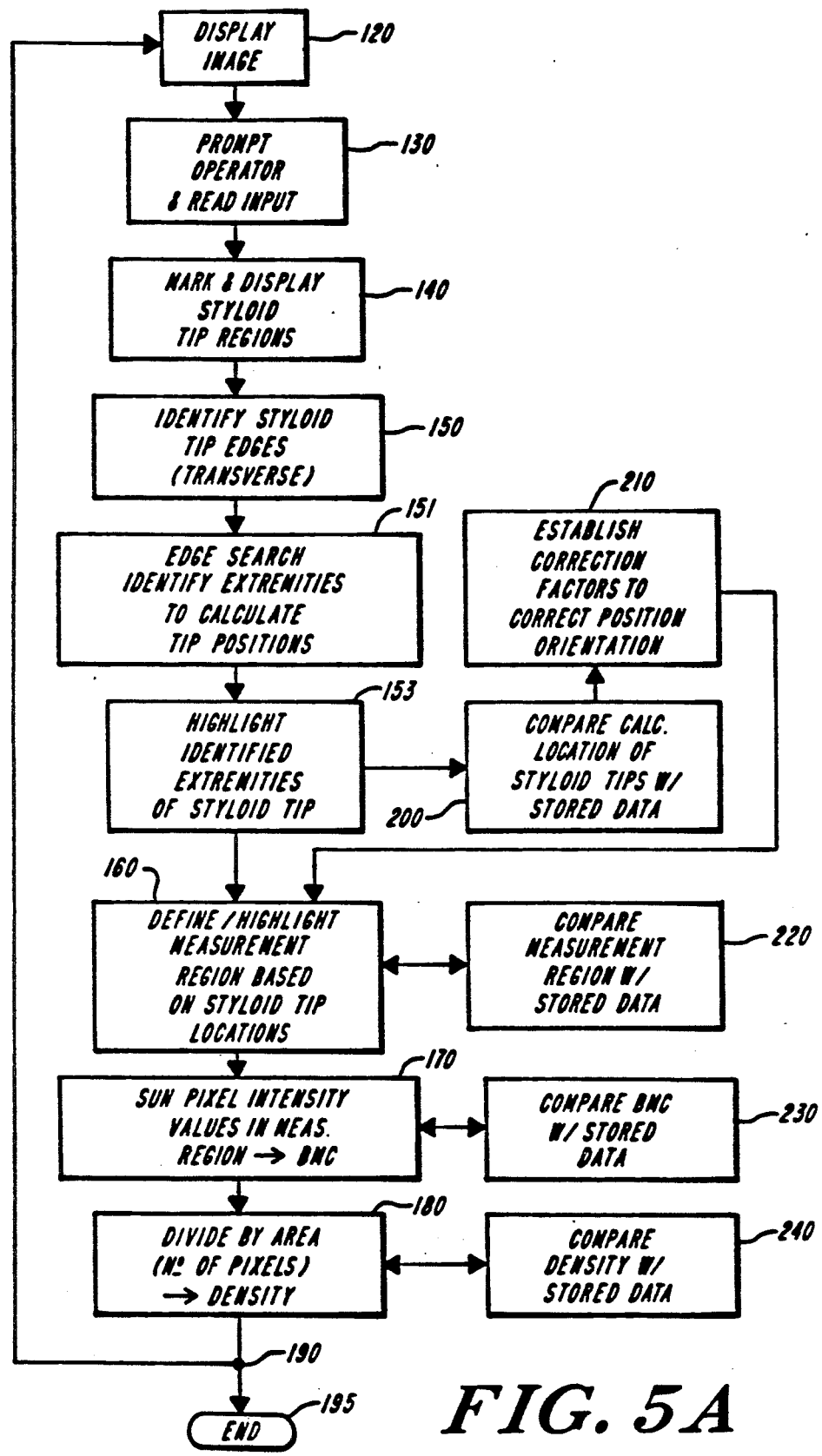
FIGS. 5A–5C are flow charts depicting a method of measuring BMC and density in accordance with the invention.
Figures 5B, 5C:
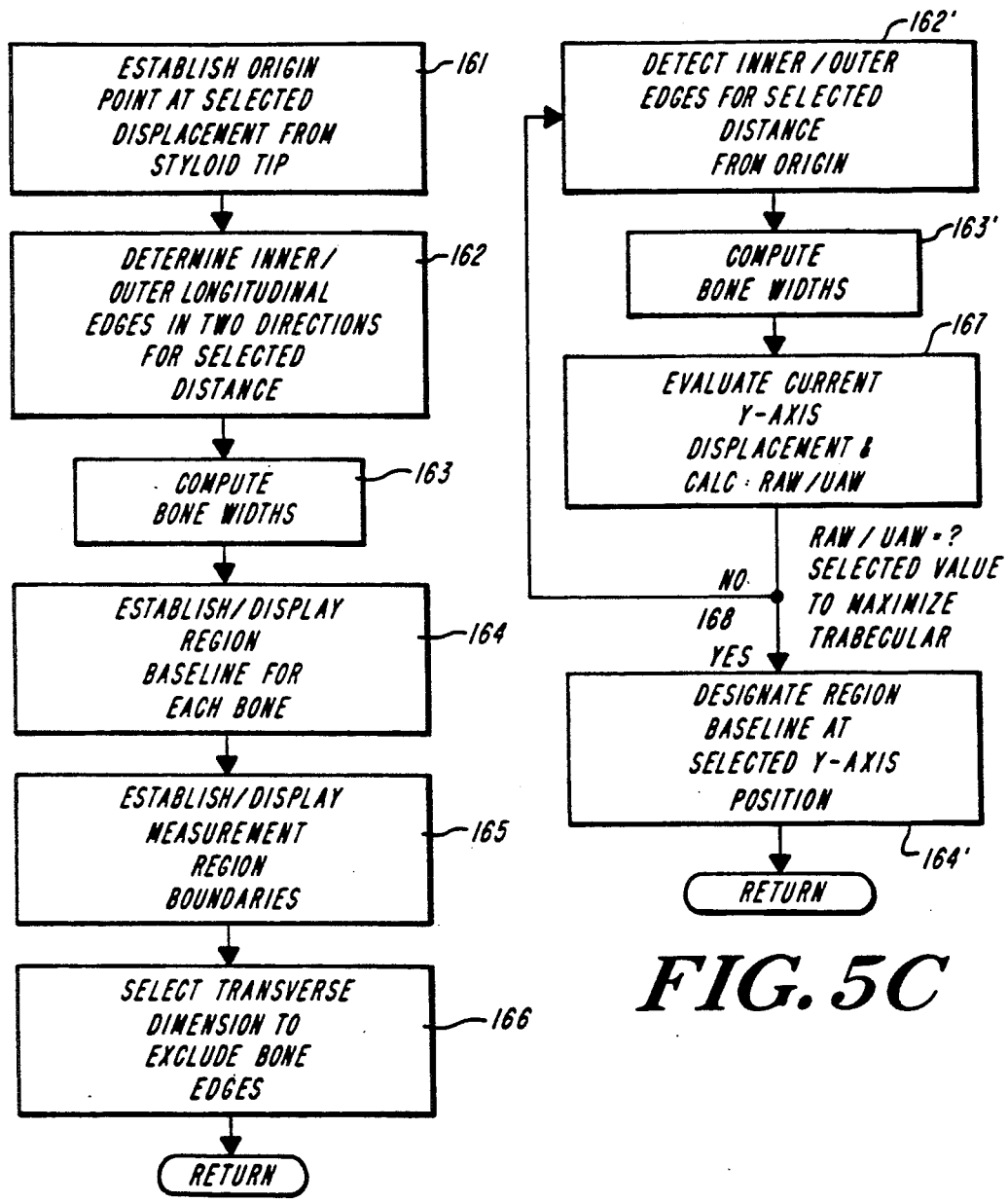

FIGS. 5A-5c illustrate the steps of a BMC measurement in accordance with the invention. These steps can be executed by data processing module 124 illustrated in FIG. 1C, which receives data from detector 114 via data acquisition module 122. In step 120 indicated in FIG. 5A, a bone joint image is displayed to an operator via a conventional monitor, such as display 126 illustrated in FIG. 1C. In accordance with conventional image generation techniques, the image presented to the operator is composed of pixels having gray level or color values representative of detector response at a given area of the bone joint being scanned. Images can be displayed in realtime from data obtained during the measurement cycle, or can be generated from data stored in conventional storage devices indicated by module 128 in FIG. 1C, which can include random access memory (RAM) or magnetic or optical disk or tape media.

The resolution of the display is not critical, as long as the bone edges are identifiable by the operator. Images can be presented in a format having 512 by 512 pixels, 256 by 256 pixels, or any arbitrary number of pixels sufficient to provide a complete display of the bone joint being imaged. Moreover, each pixel can be square or rectangular, and the width and length of each pixel corresponds to a given dimensional value in the bone joint.

In step 130 shown in FIG. 5A, the operator is prompted to use a cursor control or pointing device—such as pointing device 130 indicated in FIG. 1C, which can include a conventional mouse or joystick—to position styloid tip region markers around the respective styloid tips of the radius and ulna. These markers may include, for example, hollow rectangular region markers, similar to styloid tip region markers 25 and 26 shown in FIG. 6, which depicts a radiological image of a human left wrist. In the illustrated embodiment, a data processing unit or other computational device, such as processor 124 in FIG. 1C, executing the method steps of the invention, positions the styloid tip region markers (step 140) and reads the position of the styloid tip region markers to generate initializing data for locating the styloid tips, in accordance with known image data processing techniques.

In step 150 indicated in FIG. 5A, the location of edges surrounding the styloid tip within each marker region are determined. Bone edge finding can be implemented in accordance with any conventional edge finding algorithm, such as those disclosed in J.F. Canny, *Tech. Rep.* 720, Artificial Intell. Lab., M.I.T. (1983); "A Computational Approach to Edge Detection", *IEEE Trans. Pattern Anal. Machine Intell.*, vol. PAMI-8 (1986); F. Bergholm, "Edge Focusing", *IEEE Trans. Pattern Anal. Machine Intell.*, vol. PAMI-9 (1987). Preferred edge finding algorithms include those which reduce noise contributions in images and optimize the locating of single edges rather than multiple spurious edges which can arise in images having significant noise components.

In particular, the edge finding algorithm can be one which scans the image data represented by the pixels contained in the styloid tip region marker in a raster fashion to locate imaged bone edges. The edge finding algorithm can then compute the derivatives of vectors along each edge to determine whether a given edge belongs to the styloid tip in question. In particular, the magnitude, direction, and sign of the directional derivatives for each edge uniquely identify the edges that correspond to the styloid tip, as distinguished from other bone edges in the immediate vicinity of a styloid tip, which will have a different set of directional derivatives. This directional derivative technique is well known to those skilled in the art.

This edge finding step is followed by a positional search (step 151) executed on the edges of the styloid tip to identify one or more pixels that define the extremity of the styloid tip on each bone. Because the precise point-by-point shape of the respective radius and ulna styloid tips can differ from individual to individual, it can be useful to employ more than one form of positional search or curve fitting routine to determine the extremity of each styloid tip. The search or curve fitting routine can include a technique which finds the minimum-gradient tangent between points defining the edge, or one which locates the intersection of curves fitted to the styloid tip edges.

In the tangent method, the gradient defined by two or more points along the edge of the bone is evaluated until the gradient and the first derivative of the gradient attain a minimum value. The intersection-of-curves approach involves identifying three or more points on a given bone edge and fitting these points to a selected linear or non-linear curve —i.e., executing a parabolic fit. The intersection of the curves fitted to the outer and inner edges of the styloid tip identifies the styloid tip extremity. This technique can be advantageously employed for evaluating imaged styloid tips having opposing edges which terminate in a sharp intersection rather than a flattened extremity. The extremity of the styloid tip of the radius, for example, in many observed cases, terminates in a sharp point or ridge.

Figure 6:
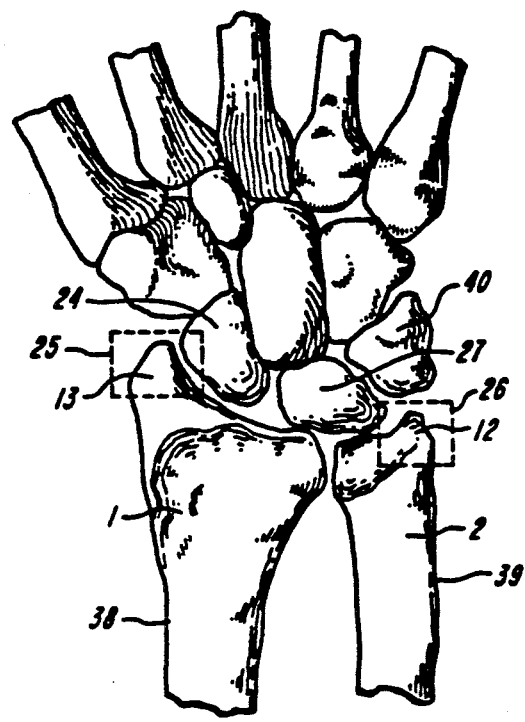
FIG. 6 depicts an imaged wrist joint and displayed marker elements around the styloid tip of the radius and ulna.

As an alternative to reading and responding to operator input to find the styloid tips, the invention can utilize known techniques for initializing edge finding on the outer edge of the radius 38 or ulna 39, and progressing up and around the styloid tips 13 and 12 to determine the edges of the styloid tip extremity. However, utilization of operator input reduces processing time, by eliminating numerous edge finding steps. Moreover, the step of responding to operator input increases accuracy over a fully automated system, because it is likely that bone edges other than those of the radius and ulna will be present within the styloid tip region of interest. This phenomenon is illustrated in FIG. 6, wherein the edges of the scaphoid bone 24 near the radius, and the lunate bone 27 and pisiform 40 bone near the ulna, are proximate to the styloid tips 13 and 12.

When the styloid tip locations have been determined, one or more pixels identified as the extremity of the styloid tip of each bone can be highlighted on the display for inspection by the operator, to confirm proper identification of the styloid tips. This is indicated in FIG. 5A as step 153.

The process then enters step 160 shown in FIG. 5A, in which measurement regions are defined based on the position of each styloid tip. In particular, further edge finding is executed to determine the outer and inner longitudinal edges of radius and ulna. This edge finding is indicated in FIG. 5B at blocks 161 and 162, which illustrate the operations comprised by step 160 of FIG. 5A. In a preferred embodiment of the invention, this longitudinal edge finding begins at an initial position, or origin point, having a selected displacement along the bone from the styloid tip (step 161), and progresses in both longitudinal directions for a selected distance (step 162). The term "longitudinal direction" is defined as the direction corresponding to the long axis of the bone. The long axis, in turn, defines a Y coordinate axis in an X—Y plane formed by orthogonal X and Y coordinate axes.

The initial start position can be, for example, 3 centimeters from the styloid tip extremity. The initial position is preferably selected to ensure that edge finding occurs in a region having an interosseous gap between radius and ulna. In particular, with the wrist in a neutral position—i.e., with no twisting of the wrist off an X-Y reference plane and the forearm positioned on the reference plane—the interosseous separation between the ulna and radius can range from approximately 0.0-2.5 centimeters, depending upon the size and shape of the bones. Initiating edge finding at a selected displacement—for example, approximately 3 centimeters—from the extremity of the styloid tip of the radius insures that edge finding will occur in a region having a gap between radius and ulna.

Longitudinal edge finding (step 162 of FIG. 5B) thus progresses along the bone from the initial start position for a selected distance in the direction of the styloid tip, and from the initial position for a selected distance in the opposite direction, to identify the edges of the bone on either side of the initial position. The selected distance can be, for example, 2 centimeters or less from the initial position.

Figure 7A:
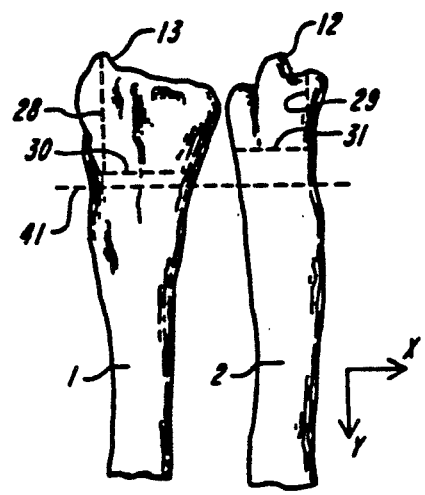
FIG. 7A depicts transverse and axial elements used to define a measurement region in accordance with the invention.

As illustrated in FIG. 7A, the longitudinal edge finding technique can be initiated by scanning the imaged bone joint across a row of pixels having a constant Y-axis position—corresponding to the selected initial position displacement from the styloid tip extremity—beginning at a X-axis position typically 1 cm outside of the X-axis position of the extremity of the radius styloid tip. The processor executing the method can test for whether three edge points are detected in a row of pixels extending to the X-axis position of the extremity of the ulna styloid tip 41. Edge points can be defined by a decrease of 20% or more in the observed intensity from a tissue baseline of three data points that is constant to within 5% or less. Failure to find three edges causes another iteration of the X-axis scan at a next Y-axis position, until an interosseous gap at a given Y-position is determined to exist.

In a preferred embodiment of the invention, if the inner edges of the ulna and radius meet within the region defined by the predetermined distance from the initial position, edge finding in the direction of the styloid tip can be terminated short of the predetermined distance. Overlap of the inner edges can be identified, for example, by the values of the directional derivatives computed in the edge finding process. Preferably, a method executed in accordance with the invention will confirm the presence of an interosseous gap before commencing longitudinal edge detection.

When longitudinal edge finding is complete, the widths of each bone are computed, in step 163 of FIG. 5B, at selected Y-axis positions. These selected Y-axis positions lie between the Y-axis positions corresponding to the smallest and largest interosseous separations, consistent with the lengths of the bone edges determined in step 162.

A horizontal line, referred to as a "region baseline", is then established and displayed (step 164 of FIG. 5B) on each bone at a Y-axis position having a selected displacement from the extremity of the respective styloid tip.

Figure 7B:
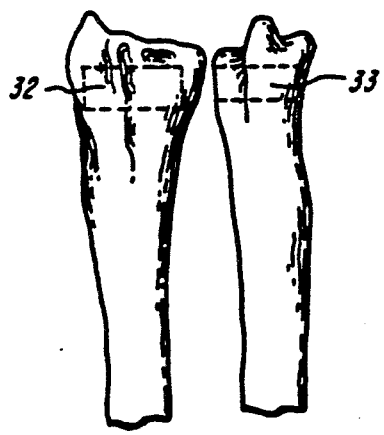
FIG. 7B depicts full-width and narrowed measurement regions utilized in accordance with the invention; and, FIG. 7C depicts deflection of the radius and ulna caused by, movement of the wrist and arm.

Using the respective baselines established in step 164 of FIG. 5B, and the bone widths calculated in step 163 of FIG. 5B, a BMC measurement region is established, as indicated in block 165 of FIG. 5B. Also in step 165, the measurement regions on each bone can be highlighted on the display for inspection by the operator. As illustrated in FIG. 7B, these measurement regions 32 and 33 can be, for example, rectangular in form, having a selected height, and a selected width based on the bone widths calculated in step 163 of FIG. 5B. In particular, the measurement regions can extend from bone edge to bone edge, as does measurement region 33 in FIG. 7B. Alternatively, by executing step 166 of FIG. 5B, the measurement regions can be reduced in width by a selected amount, to eliminate the outer and inner edges of the imaged bone from the BMC measurement region. Area 32 shown in FIG. 7B is an example of a narrowed measurement region. In many cases, narrowing the measurement region reduces inaccuracies in measurement and computation which, in some cases, result from highly irregular bone shapes, and provides increased sensitivity in BMC measurements.

Returning to FIG. 5A, in step 170, a BMC value is calculated from the image data for the measurement region defined for each bone. The BMC values can be derived in a known manner, by summing pixel intensity values in each measurement region. Bone density values can also be obtained (step 180), by dividing the BMC value by the size of the measurement regions. The area covered by the measurement regions is proportional to the number of pixels in the measurement regions. Those skilled in the art will appreciate that BMC values can be calculated from the sum of the values of the data points in the measurement region, which are in turn represented by the pixel intensity values in the measurement region. In particular, the intensity value of each pixel is proportional to the magnitude of radiation received by the detector in the region corresponding to that pixel.

As indicated in blocks 190 and 195, processing can be terminated when BMC and density values have been obtained. Alternatively, the process can be re-initialized for processing of additional radiological images.

The invention thus provides significant automation of BMC computation, including automated bone edge location. This automation of edge finding eliminates the probability of operator error in identifying bone edges.

In a preferred embodiment of the invention, enhanced rapidity and repeatability in selection of bone measurement regions, and greater sensitivity in measurement, is provided by employing a geometrical ratio—referred to as the axial/width (AW) ratio—for controlling the selection of measurement regions. In particular, referring to FIG. 7A, the radius AW (RAW) and ulna AW (UAW) ratios are equal to the Y-axis (axial) displacement 28,29 from the styloid tip at the selected measurement regions of the radius and ulna, respectively, over the bone widths 30, 31 at the selected measurement regions.

RAW values between 0.8 and 1.0, and UAW values between 0.4 and 0.8, have been observed to correlate with regions of high trabecular bone content. Utilization of these two AW ratios to control selection of measurement regions permits the selection of measurement regions having high trabecular bone content, independent of the geometrical effects caused by edges. Thus, employment of these ratios reduces the measurement inaccuracies caused by the bone spurs and edge irregularities found in many patients.

In a preferred practice of the invention, therefore, as depicted in the flowchart of FIG. 5C, these predetermined RAW and UAW values control the selection of the baseline for each measurement region. In particular, as the outer and inner edges of each bone are identified (step 162') and bone widths are calculated at successive Y-axis positions (step 163'), these width values can be continuously compared with the current Y-axis displacement 28, 29 from the known Y-axis value of the extremity of the styloid tip for each respective bone (steps 167 and 168 of FIG. 5C). The Y-axis position where the ratio of Y-axis displacement to calculated bone width satisfies the predetermined value of RAW or UAW, respectively, is designated for the measurement region baseline (step 164' of FIG. 5C). Then, as described above, the measurement region can be established upon this baseline, with a selected height and width. A typical measurement region height is 5 to 6 millimeters. The top and bottom width of the measurement region, such as region 33, can be defined by the edges of the bone, or the region can be narrowed to exclude the bone edges, as in region 32.

Moreover, in a preferred practice of the invention, illustrated in the flowchart of FIG. 5A, in successive bone mineral measurements of the same patient, currently generated image data can be compared with a previously stored image. Thus, in step 200 indicated in FIG. 5A, a comparison is made between the current orientation of the radius and ulna, and the orientation of the radius and ulna represented by stored data. This data can be stored, for example, in a magnetic or optical medium, and can represent a previously generated bone joint image used to evaluate bone mineral content.

In a further preferred embodiment of the invention, a correction factor is established for the X and Y coordinate axes (step 210 of FIG. 5A), to correlate previously generated and currently generated images and to correct small errors in positioning of the patient's forearm. Two-dimensional images, such as the bone joint images processed in accordance with the invention, have a defined orientation within an X-Y orthogonal coordinate axis system. In accordance with conventional imaging practice, pixel rows and columns correspond to coordinate axes in the X-Y coordinate system. Therefore, differences in the orientation of the ulna and radius in successive images can be detected with reference to the X-Y coordinate system.

Figure 7C:
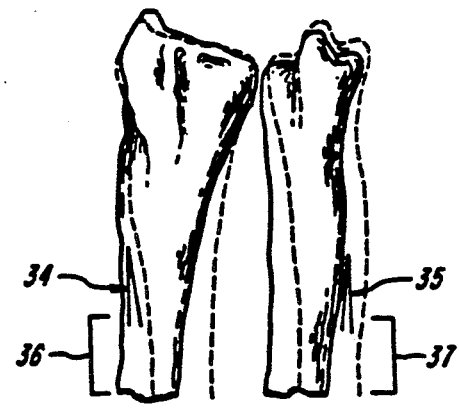

In particular, referring to FIG. 7C, the outer edges of the radius and ulna are substantially flat at a distance of 3 to 5 centimeters from the styloid tips 36, 37, respectively. The correlation and correction step of the invention therefore evaluates the gradient at various points along the outer edges of each bone, to identify the flattest portion of the outer edge of each bone. In many instances, the flat portion of the bone edge can be curve-fitted to a straight line. The curve-fitted portions of the currently generated and previously generated bone joint images are then compared to determine whether small translations and rotations of the imaged bones have occurred. This is illustrated in FIG. 7C, in which the outline of a previously generated bone joint image is indicated by dashed lines.

While translational transformations in the direction of the Y-axis do not significantly affect the repeatable selection of measurement regions in successive images, rotational transformations should be corrected from image to image. Therefore, referring again to FIG. 7C, corrections for rotational transformations are provided in accordance with the invention, by computing, using conventional image data processing techniques, the angle 34, 35 between the flat portion of the outer bone edges for each of first and second images. Based upon this computed angle, corrections for both the X- and Y-axis positional pixel values can be provided by known computational methods (step 210 of FIG. 5A). Evaluation of these angles, and of the positional values of the extremities of the styloid tips, permits images to be superposed, or otherwise placed into point-for-point registration, to insure that the vertical and horizontal bone distances are consistent from image to image for a given individual.

The above described method can be practiced in connection with conventional computational apparatus indicated by module 124 in FIG. 1C, including mainframe computers, personal computers, microprocessors, and other digital or analog computational devices. The invention is preferably implemented in a computational system having a graphic display 126 (FIG. 1C) and a simple user interface device such as a mouse or joystick 130 (FIG. 1C). Additionally, the invention can be advantageously practiced in connection with computer apparatus including magnetic or optical storage devices 128 (FIG. 1C), such as tapes or disks, for storing values representative of the position of the extremities of the styloid tips, the coordinates of the measurement regions, the orientation of bones, and other image data, for future use in BMC evaluations.

It will thus be seen that the invention efficiently attains the objects set forth above, among those made apparent from the preceding description. In particular, the invention provides a method for consistently and repeatably establishing BMC measurement regions in bone areas having high trabecular bone content. The invention also provides the capabilities of detecting positional differences from image to image, and of correcting for such positional differences to enable accurate comparisons of BMC values.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A method for determination of bone mineral content from a radiological image of a bone joint, the bond joint including at least a first bone having a styloid tip, the method comprising the steps of
    imaging the bond joint to obtain an image composed of individual pixels having varying intensity values,
    identifying the position of the styloid tip of the bone in said image, and
    defining at least a first measurement region having a selected area and located at a selected distance from said position of the styloid tip, in which region the joint has a bone structure suitable for measurement of bond mineral content.

2. A method according to claim 1, further comprising determining a pixel intensity sum within the measurement region and dividing said sum by a value representative of the area of the measurement region to obtain a representation of bond density.

3. A method according to claim 1, further comprising the step of retrieving a previous image of the bone joint and comparing said previous image with a newly-obtained image to obtain a positional correlation of the bone in said previous and newly-obtained images.

4. A method according to claim 3, further comprising the step of calculating axial and transverse correction factors for correcting differences in position of the bone in currently and previously displayed images.

5. A method according to claim 4, wherein said step of calculating axial and transverse correction factors includes the step of comparing positions of the styloid tip in the currently and previously displayed images.

6. A method according to claim 5, further comprising the step of storing, in the storage elements, said pixel intensity sum representative of bone mineral content.

7. A method for determining the bone mineral content of a bone joint, comprising the steps of
    imaging the bone joint to obtain an image composed of individual pixels having varying intensity values,
    displaying said image of said bone joint,
    responding to operator input to display markers surrounding a displayed styloid tip,
    locating said position of the styloid tip within a region bounded by said display markers, and
    defining at least a first measurement region having a selected area and located at a selected distance form said position of the styloid tip, in which region the bone joint has a bone structure suitable for bone mineral content measurement.

8. A method according to claim 7, further comprising the step of displaying, in highlighted form, said measurement region.

9. A method for determining the bone mineral content of a bone joint, comprising the steps of:
    imaging the bone joint to obtain an image composed of individual pixel shaving varying intensity values,
    locating the position of the styloid tip of the bone in said image, the locating step further comprising:
        detecting selected transverse image edges, said transverse image edges being transverse to a long axis of the bone,
        searching along said selected transverse image edges to determine a set of pixels which define extremities of the styloid tip, and
        defining a tangent line corresponding to, and substantially tangent to, the styloid tip, and
    defining at least a first measurement region having a selected area and selected positional correspondence to said position of the styloid tip, 10. A method according to claim 9, wherein said step of searching along said selected transverse image edges includes the step of detecting a succession of pixels, along said selected transverse image edges, having minimum slope.

11. A method according to claim 9, wherein said step of searching along said selected transverse image edges includes the step of determining an intersection of curves fitted to the edges of the styloid tip.

12. A method according to claim 9, further comprising the step of displaying, in highlighted form, said set of pixels defining the extremities of the displayed styloid tip.

13. A method according to claim 9, wherein said step of defining measurement region includes the step of defining a baseline for said measurement region, said baseline being substantially parallel to, and separated by a selected distance from, said tangent line.

14. A method according to claim 13, wherein said step of defining said baseline includes the step of defining said baseline to be separated by approximately 8–15 millimeters from said tangent line.

15. A method according to claim 13, wherein said step of defining a measurement region further includes the step of detecting outer and inner axial edges of the bone, said axial edges being substantially parallel to a long axis of the bone.

16. A method according to claim 15, wherein said step of detecting outer and inner edges includes the step of detecting said outer and inner axial edges for selected axial distances along the bone, starting at an origin point separated by a selected distance from said tangent line.

17. A method according to claim 16, wherein said step of detecting outer and inner edges includes the step of detecting said outer and inner edges for a distance of approximately 1–3 centimeters in either axial direction from an origin point approximately 1–3 centimeters from said tangent line.

18. A method according to claim 15, further comprising the step of utilizing said detected outer and inner edges to compute transverse width values for the bone, at positions along the bone between points of minimum and maximum interosseous separation.

19. A method according to claim 15, wherein said step of defining a measurement region further includes the step of defining said measurement region to have a selected axial dimension and to include said inner and outer axial edges.

20. A method according to claim 15, wherein said step of defining said measurement region further includes the steps of
   defining said measurement region to have a selected axial dimension and
   narrowing said measurement region to exclude said inner and outer axial edges.

21. A method according to claim 13, wherein said step of defining baseline includes the steps of
   calculating ratios of axial-separation-from-tangent-line to width (AW ratios) at positions along the bone, and
   defining said baseline for said measurement region to be at a position having a selected AW ratio.

22. A method according to claim 21, further comprising the step of selecting AW ratios to define a measurement area having maximum trabecular bone content.

23. Digital processing apparatus for repeatable calculation of bone mineral content from a radiological image of a bond joint comprising
   imaging means for imaging a bone having a styloid tip to obtain a bone image composed of individual pixels having varying intensity values,
   locating means for locating the position of the styloid tip, and
   definitional means for defining at least a first measurement region having a selected area and located at selected distance from said position of the styloid tip, in which region the joint has a bone structure suitable for bone mineral content measurement.

24. Apparatus according to claim 23, further comprising means for summing said pixel intensity values to obtain a intensity sum within said measurement region and means for dividing said pixel intensity sum by a value representative of the area of said measurement region, to yield a value representative of bone density.

25. An apparatus for determining the bone mineral content of a bone joint, comprising
   imaging means for imaging the bone joint to obtain an image composed of individual pixels having varying intensity values,
   locating means for locating the position of the styloid tip of the bone in said image, said locating means further comprising
      means for detecting selected transverse image edges, said transverse image edges being transverse to a long axis of the bone,
      means for searching along said selected transverse image edges to determine a set of pixels which define extremities of the styloid tip, and
      means for defining a tangent line corresponding to, and substantially tangent to, the styloid tip, and
   definitional means for defining at least a first measurement region having a selected area and selected positional correspondence to said tangent line.

26. Apparatus according to claim 25, wherein said means for searching along said selected transverse image edges comprises means for detecting a succession of pixels, along said selected transverse image edges, having minimum slope.

27. Apparatus according to claim 25, wherein said means for searching along said selected transverse image edges comprises means for determining an intersection of curves fitted to the edges of the styloid tip.

28. Apparatus according to claim 25, further comprising means for displaying, in highlighted form, said set of pixels defining said extremities of the displayed styloid tip.

29. Apparatus according to claim 25, wherein said means for defining a measurement region comprises means for defining a baseline for said measurement region, said baseline being substantially parallel to, and separated by a selected distance from, said tangent line.

30. Apparatus according to claim 29, wherein said means for defining baseline comprises means for defining said baseline to be separated by approximately 8-15 millimeters from said tangent line.

31. Apparatus according to claim 29, wherein said means for defining a measurement region further comprises means for detecting outer and inner axial edges of the bone, said axial edges being substantially parallel to a long axis of the bone.

32. Apparatus according to claim 31, wherein said means for detecting outer and inner edges comprises means for detecting said outer and inner axial edges for selected axial distances along the bone, starting at an origin point separated by selected distances from said tangent line.

33. Apparatus according to claim 32, wherein said means for detecting outer and inner edges comprises means for detecting said outer and inner edges for a distance of approximately 1-3 centimeters in either axial direction from an origin point approximately 1-3 centimeters from said tangent line.

34. Apparatus according to claim 31, further comprising means for utilizing said detected outer and inner edges to compute transverse width values for the bone, at positions along the bone between points of minimum and maximum interosseous separation.

35. Apparatus according to claim 31, wherein said means for defining a measurement region further comprises means for defining said measurement region to have a selected axial dimension and to include said inner and outer axial edges.

36. Apparatus according to claim 31, wherein said means for defining a measurement region further comprises
   means for defining said measurement region to have a selected axial dimension and
   means for narrowing said measurement region to exclude said inner and outer axial edges.

37. Apparatus according to claim 29, wherein said means for defining baseline comprises
   means for calculating ratios of axial-separation-from-tangent-line to width, at positions along the bone, and
   means for defining said baseline for said measurement region to be at positions having selected AW ratios.

38. Apparatus according to claim 37, further comprising means for selecting AW ratios to define a measurement area having maximum trabecular bone content.

39. Apparatus according to claim 23, further comprising means for retrieving a previous image of the bone joint and comparing said previous image with a newly-obtained image to obtain a positional correlation of the bone in said previous and newly-obtained images.

40. Apparatus according to claim 39, further comprising means for calculating axial and transverse correction factors for correcting differences in the position of the bone in currently and previously displayed images.

41. Apparatus according to claim 40, wherein said means for calculating axial and transverse correction factors comprises means for comparing the position of the styloid tip, in said currently and previously displayed images.

42. Apparatus according to claim 41, further comprising means for storing, in said storage elements, data representative of bone mineral content.

43. Apparatus for determining the bone mineral content of a bone joint, comprising imaging means for imaging the bone joint to obtain an image composed of individual pixels having varying intensity values, display mans for displaying said bone joint image, locating means for locating the position of the styloid tip of the bone in said image, the locating means further comprising marking means for responding to operator input to display markers surrounding a displayed styloid tip, and identifying means for identifying said position of the styloid tip within a region bounded by said display markers, and definitional means for defining at least a first measurement region having a selected area and located at a selected distance from said position of the styloid tip, in which region the bone joint has a bone structure suitable for bone mineral content measurement.

44. Apparatus according to claim 43, further comprising means for displaying, in highlighted form, said measurement region.

* * * * *